United States Patent
Belk et al.

(10) Patent No.: US 6,198,834 B1
(45) Date of Patent: Mar. 6, 2001

(54) MEAT IMAGING SYSTEM FOR PALATABILITY YIELD PREDICTION

(76) Inventors: Keith E. Belk, 2217 Brixton Rd., Fort Collins, CO (US) 80526; Joseph Daryl Tatum, 4410 Monte Carlo Dr.; Gary C. Smith, 1102 Seton St., both of Fort Collins, CO (US) 80525; Martin Goldberg, 4341 Cub Run Rd., Chantilly, VA (US) 20151; Aaron M. Wyle, 612 E. Pitkin, Fort Collins, CO (US) 80524; Robert C. Cannell, 1363 Autum Ash Ct., Loveland, CO (US) 80538

( * ) Notice: Subject to any disclaimer, the term of this patent is extended or adjusted under 35 U.S.C. 154(b) by 0 days.

(21) Appl. No.: 09/377,481

(22) Filed: Aug. 19, 1999

Related U.S. Application Data

(63) Continuation of application No. PCT/US99/03477, filed on Feb. 18, 1999.
(60) Provisional application No. 60/075,517, filed on Feb. 20, 1998.

(51) Int. Cl.[7] .................................................. G06K 9/00
(52) U.S. Cl. ............................................. 382/110; 348/89
(58) Field of Search ..................................... 382/110, 128, 382/131; 348/89; 452/158; 426/231

(56) References Cited

U.S. PATENT DOCUMENTS

| 4,226,540 | 10/1980 | Barten et al. ................... 356/445 |
| 4,413,279 | 11/1983 | Görl ................................... 358/107 |
| 5,339,815 | * 8/1994 | Liu et al. ........................ 128/660.01 |
| 5,398,290 | 3/1995 | Brethour ............................... 382/6 |
| 5,474,085 | 12/1995 | Hurnik et al. ..................... 128/774 |
| 5,668,634 | * 9/1997 | Newman ............................. 356/445 |
| 5,944,598 | * 8/1999 | Tong et al. .......................... 452/158 |
| 5,960,105 | * 9/1999 | Brethour ............................ 382/141 |

FOREIGN PATENT DOCUMENTS

| 2187281 | 9/1987 | (GB) | G01N/33/12 |
| WO93/21597 | 10/1993 | (WO) | G06F/15/70 |
| WO 94/00997 | 1/1994 | (WO) | A22B/5/00 |
| WO 94/02803 | 2/1994 | (WO) | G01B/7/06 |
| WO 95/21375 | 8/1995 | (WO) | G01N/21/27 |
| WO95/21375 | 8/1995 | (WO) | G01N/21/27 |
| WO 97/18468 | 5/1997 | (WO) | G01N/33/12 |

OTHER PUBLICATIONS

Abouelkaram et al., "Quantitative Ultrasonic Assessment of Tissue Macroscopic Heterogeneity," Proc. IEEE 1992 Ultrasonics Symposium, Oct. 20–23, 1992, pp. 1053–1056.*

Amin et al., "Application of Neural Network in Ultrasound Tissue Characterization Using Backscattered Signal Parameters," Proc. 1992 IEEE Nuclear Science Symposium and Medical Imaging Conf., Oct. 25–31, 1992, pp. 1357–1359.*

Hein et al., "Ultrasound Data Acquisition System Design for Collecting High Quality RF Data from Beef Carcasses in the Slaughterhouse Environment," Proc. IEEE 1992 Ultrasonics Symposium, Oct. 20–23, 1992, pp. 1039–1044.*

Amin et al., "Tissue Characterization for Beef Grading Using Texture Analysis of Ultrasonic Images," Proc. IEEE 1993 Ultrasonics Symposium, Oct. 31–Nov. 3, 1993, pp. 969–972.*

(List continued on next page.)

Primary Examiner—Andrew W. Johns
(74) Attorney, Agent, or Firm—Howery Simon Arnold & White, LLP

(57) ABSTRACT

An image analysis (IA) system for scoring characteristics predictive of palatability and yield of a meat animal carcass or cut. The IA system uses an imaging device, a data processing unit for processing image data, and an output device for output of processed data to the user. Also disclosed is a method for using the IA system in predicting palatability, yield, or defect conditions of a meat animal carcass or cut. The results are identified with a particular piece of meat for further grading, sortation and processing.

42 Claims, 3 Drawing Sheets

OTHER PUBLICATIONS

Arul et al., "Characterization of Beef Muscle Tissue Using Texture Analysis of Ultrasonic Images," IEEE Proc. 12th Southern Biomedical Engineering Conf., Apr. 2–4, 1993, pp. 141–143.*

Zhang et al., "Frequency and Intensity Texture Analysis for Beef Quality Evaluation and Predition from Ultrasound Images," Proc. 16th Annual Int. Conf. of the IEEE Eng. in Medicine and Biology Soc., Nov. 3–6, 1994, pp. 668–669.*

Zhang et al., "Image Analysis and Application Systems in Quality Evaluation and Prediction for Meat and Live Meat Animals," Proc. IEEE 1994 Int. Conf. on Image Processing, Nov. 13–16, 1994, pp. 241–244.*

Wang et al., "Automated Beef Steak Grading by Digital Image Analysis," Proc. 1997 IEEE Int. Conf. on Systems, Man, and Cybernetics, Oct. 12–15, 1997, pp. 500–504.*

Wulf et al., "Using Objective Measures of Mucle Color to Predict Beef Longissimus Tenderness." *J. Anim. Sci.* 75:684–692 (1997).

Park et al., *J. Food. Sci.* 59:697–701 (1994) "Ultrasonic Spectral Analysis for Beef Sensory Attributes".

* cited by examiner

MEAT IMAGING SYSTEM FOR PALATABILITY YIELD PREDICTION

The present invention claims priority of U.S. provisional application Ser. No. 60/075,517 filed Feb. 20, 1998 and continuation of PCT application number PCT/US99/03477 filed Feb. 18, 1999.

BACKGROUND OF THE INVENTION

1. Field of the Invention

The field of the present invention is prediction of meat palatability and yield. More specifically, the present invention relates to the prediction of meat palatability and yield by use of image analysis (IA) to determine the color parameters L* (psychometric lightness), a* (red vs. green), and b* (yellow vs. blue) or the tissue density of the lean and fat portions of a meat animal carcass or cut.

2. Description of Related Art

Consumers of meat generally prefer, and are willing to pay for, greater meat tenderness. Marbling score of a carcass has been shown to generally correlate with subsequent cooked meat palatability across a wide range of marbling levels for beef, pork, and lamb. However, between carcasses with the same marbling level, there are substantial differences in palatability. Other factors of the carcass believed to predict palatability include maturity score, muscle pH, and muscle color; these factors may be more valuable in the prediction of palatability of chicken, turkey, and fish. Among those with expertise in carcass examination, e.g. meat scientists and U.S. Department of Agriculture (USDA) graders, some of these factors can be scored and palatability predicted by assigning a USDA Quality Grade, given sufficient examination time. In practice, for the example of beef, USDA graders working at packing plants commonly must assign Grades to 250 to 450 beef carcasses per hour, which does not provide enough time for a complete examination of all factors related to prediction of palatability. The shortage of time also makes difficult the required accurate computation of Quality Grades.

In addition, USDA graders are required to compute Yield Grades, which are intended to estimate the cutability and composition of a carcass. Factors used to determine Yield Grades include hot carcass weight, ribeye area (cross-sectional area of the longissimus m. at the 12–13th rib interface), estimated kidney, pelvic, and heart fat percentage, and actual and adjusted subcutaneous fat thickness at the carcass exterior. The time constraints described above for the calculation of Quality Grades also apply to the calculation of Yield Grades. The parameters that underlie the assignment of Quality Grades and Yield Grades are published by the USDA Agricultural Marketing Service, Livestock and Seed Division, e.g., for beef, the United States Standards for Grades of Carcass Beef.

A device for scoring factors predictive of palatability of a meat carcass or cut, in addition to an examination of the carcass or cut by a USDA grader would allow meat palatability to be more accurately predicted and USDA Quality Grades to be more accurately assigned. This would allow greater consumer confidence in the Quality Grading system, as well as any additional system for certification of conformance to product quality specifications, as would be desired in a "brand-name" program. In either event, more precise sortation of carcasses for determining meat prices would be allowed. This superior sortation would provide economic benefit to those at all segments of the meat production system: restaurateurs, foodservice operators, and retailers; packers; feed lot operators; and ranchers, farmers, and harvesters of pork, lamb, beef and dairy cattle, chicken, turkey, and various fish species. This superior sortation would also benefit scientists in the collection of carcass and cut data for research, and the previous owners of livestock in making genetic and other management decisions.

Several attempts have been made to construct such devices for use in the beef industry. One such device uses a "duo-scan" or "dual-component" image analysis system. Two cameras are used; a first camera on the slaughter floor scans an entire carcass, and a second camera scans the ribeye after the carcass is chilled and ribbed for quartering. In the use of these systems, video data are recorded from a beef carcass and transferred to a computer. A program run by the computer determines the percentages of the carcass comprised of fat and lean from the recorded image and additional data available, e.g. hot carcass weight. The quantities of cuts at various levels of lean that can be derived from the carcass are then predicted. However, based on scientific evaluation, the system is not able to predict palatability of the observed carcass for augmenting the assignment of a USDA Quality Grade or other purpose related to sorting carcasses based on eating quality.

One possible set of factors that can be examined to predict palatability is muscle and fat color. Wulf et al., J. Anim. Sci. (1997) 75, 684, reported results of both color scoring in the L*a*b* color space of raw *longissimus thoracis* muscle at 27 h postmortem, and Warner-Bratzler shear force determinations of aged, thawed, cooked *longissimus lumborum* muscle, from carcasses of cattle derived from crosses between various breeds of *Bos taurus* (European-based genetics) and *Bos indicus* (heat-tolerant, tropically-based genetics). Tenderness, as measured by shear force, correlated with all three color measurements, with the highest correlation seen with b* values. These results demonstrated that muscle color can be used to predict beef palatability.

Among other factors that can be examined to predict palatability are lean tissue density, fat tissue density and connective tissue density. Park et al., *J. Food. Sci.* (1994) 59:697–701, reported results of A-mode (one-dimensional brightness) ultrasonic spectral feature analysis. Tenderness correlated with resonant frequency, juiciness and flavor correlated with the number of local maxima. These results demonstrated that ultrasonic spectral features and other methods known in the art for determining tissue density can be used to predict beef palatability.

Therefore, it is desirable to have an apparatus for scoring factors predictive of the palatability of a meat animal carcass. It is desirable for such an apparatus to collect and process data and provide output within the time frame that a carcass is examined by a USDA grader under typical conditions in the packing house, commonly 5–15 sec. It is desirable for such an apparatus to return scores for at least one of, for example, color and color variability of lean tissue, color and color variability of fat tissue, extent of marbling, average number and variance of marbling flecks per unit area, average size of marbling and the variance of average marbling size, average texture, firmness of lean tissue, lean tissue density, fat tissue density and connective tissue density. It is desirable for the apparatus to use these measures to assign a grade or a score to carcasses in order that the carcasses can be sorted into groups that reflect accurate differences in cooked meat palatability. It is also desirable for the apparatus to use these measures to identify defect conditions in the meat such as, but not limited to, bruising, dark cutter or heat ring.

It is also desirable to have an apparatus for measuring the cross-sectional surface area of an exposed, cut muscle (e.g.

ribeye) for use in predicting the composition (fat, lean, bone) of a carcass or cut. It is desirable for the apparatus to use this measure to assign a grade or score to carcasses in order that the carcasses can be sorted into groups that reflect accurate differences in yield. It is desirable for this apparatus to also measure relative areas of cross-section surfaces comprised of fat and/or bone. In addition, it is desirable to have an apparatus for measuring, predicting, and sorting carcasses on the bases of any combinations of palatability, defect conditions, and yield.

Further, it is desirable for such an apparatus to be portable, e.g. small and lightweight. It is desirable for the apparatus to be capable of withstanding packing plant environments, e.g. to be mounted in a protective housing.

SUMMARY OF THE INVENTION

The present invention is related to a method for predicting the palatability of meat, comprising: providing image data related to at least a portion of the meat; analyzing the image data to distinguish at least one area of interest of the meat; analyzing the image data corresponding to each area of interest to measure at least one characteristic of the area of interest based on the image data; predicting the palatability of the meat based on the characteristic.

The present invention is also related to an apparatus for predicting the palatability of meat, comprising: an imaging device adapted to provide an image data of at least a portion of the meat; a data processing unit adapted to execute program instructions; a program storage device encoded with program instructions that, when executed, perform a method for predicting the palatability of meat, the method comprising: analyzing the image data to distinguish at least one area of interest of the meat; analyzing the image data corresponding to the area of interest to measure at least one characteristic of the lean section based on the image data; and predicting the palatability of the meat based on the characteristic.

DESCRIPTION OF ILLUSTRATIVE EMBODIMENTS

Figure 1:
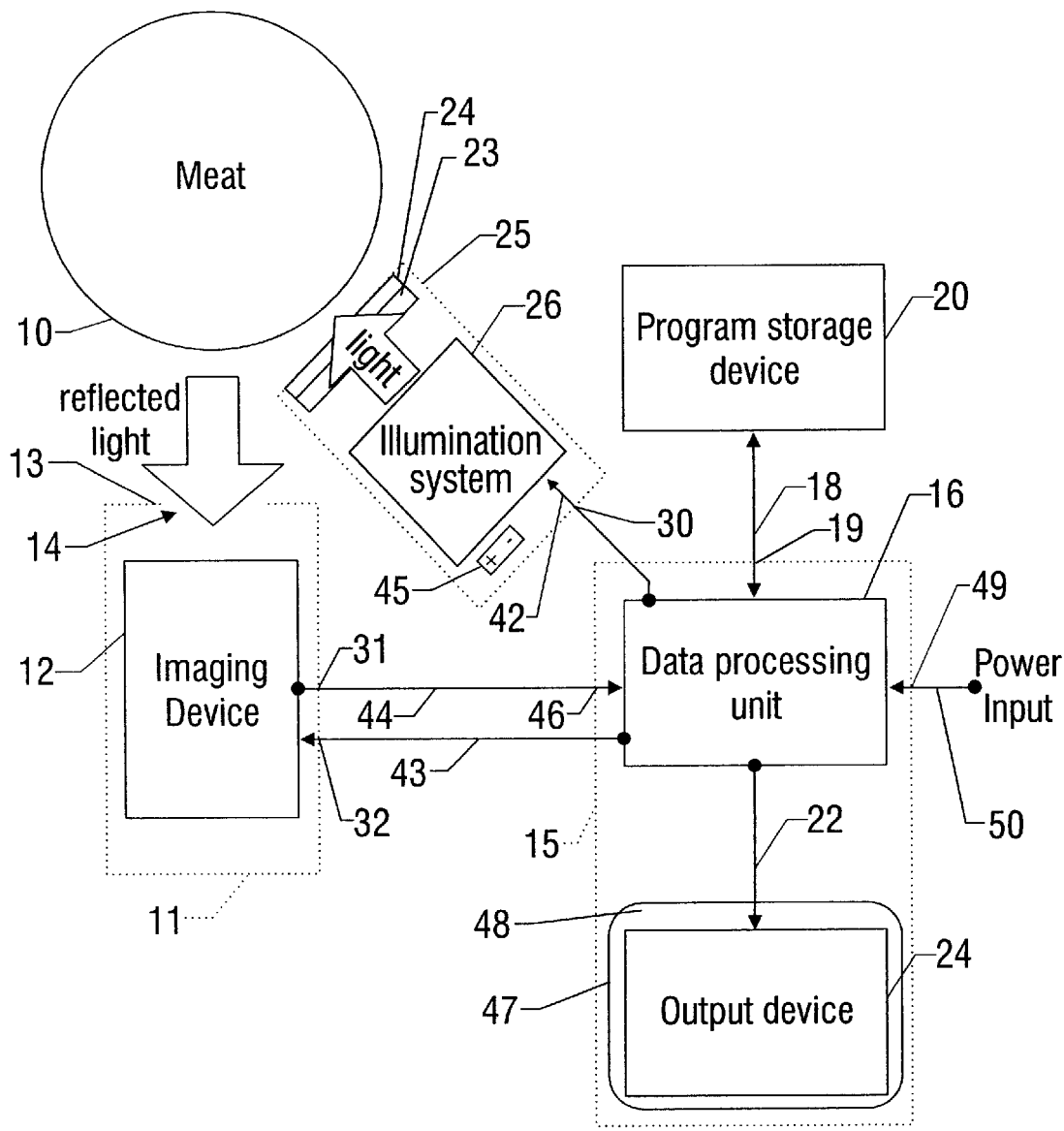
FIG. 1 shows a schematic view of an apparatus of the present invention.
Figure 2:
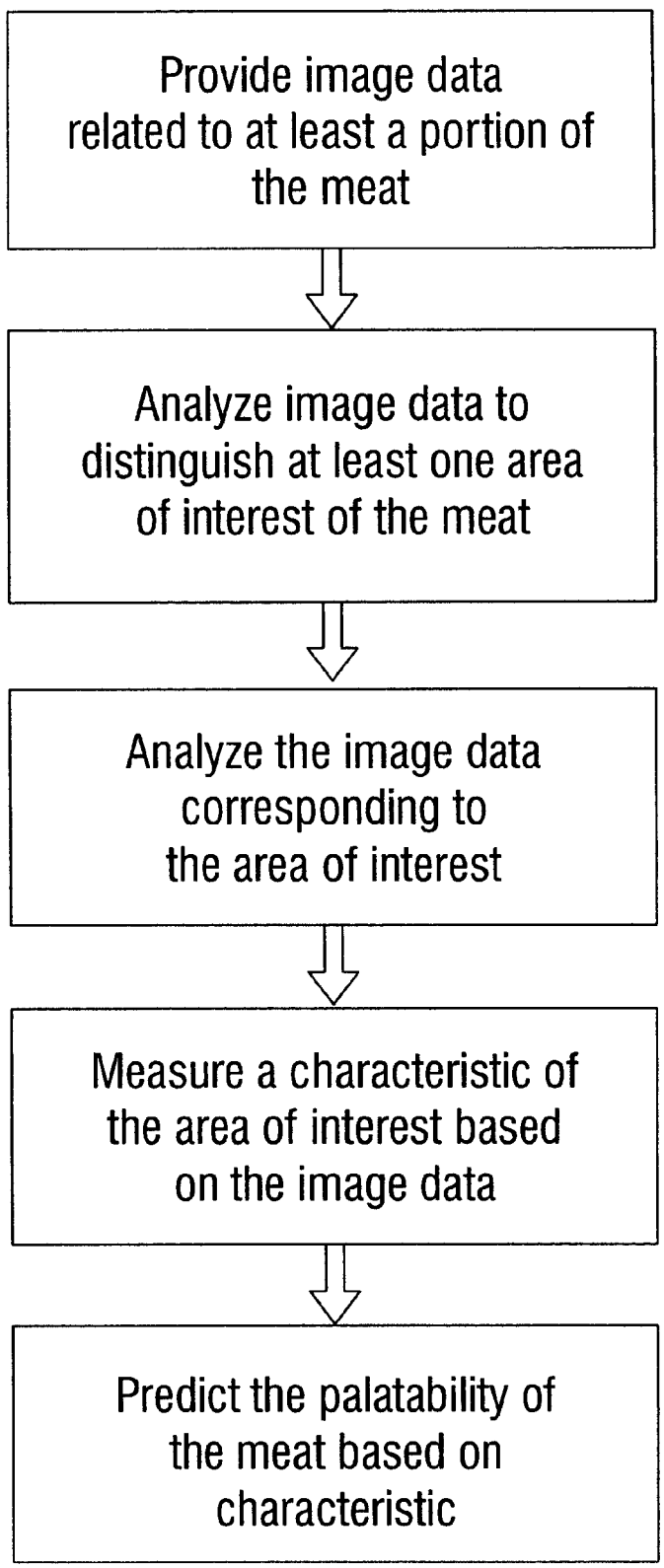
FIG. 2 shows a flowchart of a method of the present invention.

The present invention provides an image analysis (IA) system for scoring factors predictive of the palatability of a meat animal carcass. The IA system may be any type of imaging system known to those of skill in the art, such as a camera, tomographic imaging, magnetic resonance imaging (MRI), sound wave imaging, radio wave imaging, microwave imaging, or particle beam imaging, and is preferably a color video IA system. As shown in FIG. 1, the IA system includes an imaging device 12, preferably a 3-CCD color video camera, preferably mounted in an enclosures 11. The imaging device 12 optionally features an illumination system 26 mounted either on the imaging device, on the imaging device enclosure, or not on the imaging device but in the imaging device enclosure. The illumination system 26 may be any light emitting device known to those of skill in the art, or a source of energy of equivalent function meant to impinge on the sample of meat for measurement in the parts of the energy spectrum corresponding to the sensitivity ranges required by the type of imaging device 12, including visible light, infrared light, ultraviolet light, x-rays, gamma rays, electrons, positrons, electrical fields, magnetic fields, sonic wave, ultrasonic wave, infrasonic wave or microwaves. The IA system also includes a data processing unit 16, the data processing unit 16 interfaced with a program storage device 20 by a program storage device interface 18, and at least one output device 24 by an output device interface 22.

The program storage device 20 contains a computer program or programs required for proper processing of image data, preferably color video image data, by the data processing unit 16. The data processing unit 16 is linked to, and receives data from, the video camera 12 via either a transfer cable 14 or a wireless transmission device (not shown). The data processing unit 16 comprises a standard central processing unit (CPU), and, where necessary or appropriate, preferably also a software module or hardware device for conversion of analog data to digital data, and processes image data according to instructions encoded by a computer program stored in the program storage device 20. Image data can be used in subsequent calculation of the values of characteristics, the values being predictive of palatability, the characteristics including color and color variability of lean tissue, color and color variability of fat tissue, extent of marbling, average number and variance of marbling flecks per unit area, average size of marbling and the variance of average marbling size, average texture of marbling and lean tissue, firmness of lean tissue, density of lean tissue, density of fat tissue, and density of connective tissue. These values can then be used to sort meat (herein defined as a meat animal carcass, side, or cut, or any portion of a carcass, side, or cut) into groups that vary in predicted subsequent cooked eating quality.

The color parameters L*, a*, and b*, or the tissue density parameters can also be used to calculate the values of factors predictive of yield, such as the cross-sectional area of a muscle of interest and other surrounding organs such as fat, bone, and connective tissue. These values can then be used to sort meat into groups that vary in predicted composition.

The color parameters L*, a*, and b* can also be used to calculate the values of factors predictive of defect conditions of the meat, such as bruising, dark cutter and heat ring. These values can then be used to denote the carcass as defective or to adjust or otherwise alter the quality sortation decision.

The data processing unit 16 is linked to, and transmits results of data processing to, at least one output device 24 by output device interface 22. Optionally, results of data processing can also be written to a file in the program storage device 20 via program storage device interface 18. An output device 24 can be a video screen, printer, or other device. It is preferred that at least one output device 24 provide a physical or electronic tag to label the meat 10 with results of data processing, in order to facilitate sortation of meat animal carcasses, cuts, or both into groups with similar predicted palatability and/or yield.

The present invention also provides a method of predicting the palatability of the meat 10 and determining the cross-sectional area of the meat 10. Using the color IA system referred to above, image data collected from meat 10 is recorded by the imaging device 12, processed by the data processing unit 16, and the values of palatability and/or muscle cross-sectional area is output by the output device 24 to augment the observations made by a USDA line grader, or other operator responsible for sorting or characterizing meat animal carcasses, in order to allow more accurate assignment of Quality Grades, Yield Grades, defect conditions, and/or other sorting or classification criteria based on the characteristics.

An apparatus for use in the present invention comprises an imaging device 12 and a data processing unit 16. The imaging device 12 can be any such imaging device known to those of skill in the art, such as a camera, tomographic imaging (i.e. CAT, PET) device, magnetic resonance imaging (MRI) device, sound wave imaging device, radio wave imaging device, microwave imaging device, or particle beam imaging device. If the imaging device is a camera, the camera is at least one of a photographic camera, a digital still camera, and a video camera. The camera responds to light in at least one portion of the light spectrum, each such portion consisting of a band of, such as a segment of ultraviolet wavelengths (200 nm to 400 nm), visible wavelengths (400 nm to 700 nm), infrared wavelengths (700 nm to 10 m), or portions thereof.

If the image is tomographic, it can be obtained by at least one of x-ray tomography, and particle beam tomography, such as computer axial tomography (CAT) or positron emission tomography (PET). These devices produce non-invasive cross-sectional and three-dimensional images resulting from the transmission and scattering characteristics of the specimen to the type of incident energy, where intensity is a function of object cross-sectional density.

If the image is a sound wave image, it can be obtained by ultrasound, B-mode ultrasound, or infrasonic imaging. These devices produce non-invasive cross-sectional and three-dimensional images resulting from the transmission and reflection characteristics of the specimen to the frequency of sound wave applied, where intensity is a function of object cross-sectional density.

It is important for the imaging device 12 to provide output within the time frame allotted for meat carcass examination, typically 5–15 seconds. Preferably the output is in real-time. Such real-time output can be the same technology as the viewfinder on a known camcorder or video camera, the real-time output can be the same technology as a known digital camcorder, the real- time output can be a known computer-generated real-time display as are known in video-conferencing applications, or can be any other technology known to those of skill in the art. It is preferable for the imaging device 12 to be a color video camera, for reasons discussed below. It is also preferred that the imaging device 12 be small and lightweight, to provide the advantages of portability and flexibility of positioning, i.e. adjusting the camera angle by the user to provide for optimal collection of image data from the meat 10. It is also preferred the imaging device 12 be durable, in order to better withstand the environment of the packing plant. The power source of the imaging device 12 can be either direct current, i.e. a battery secured to electrical contacts from which the imaging device 12 can draw power, or alternating current provided from either an electrical outlet or from the data processing unit 16.

An illumination system 26 can optionally be used to illuminate the meat with energy in the useful spectrum of the imaging device. This is desirable when using visible light imaging and the ambient lighting is poor or uneven or when it is desired to examine regions of the meat 10 that are not illuminated by ambient light, or when the spectral sensitivity of the imaging device is not in the visible light part of the electromagnetic spectrum. Any known or future developed illumination system 26 can be used, e.g. a lamp (incandescent, fluorescent, etc.), a laser, etc. for visible and near-visible portions of the spectrum, x-rays, gamma rays, electrons, electrical fields, magnetic fields, sonic beam, ultrasonic beam, infrasonic beam, or microwaves. The power source 42 of the illumination system 26 can be either direct current, i.e. a battery 45, or alternating current drawn from either an electrical outlet 50, the imaging device 12, or the data processing unit 16. It is preferred that the illumination system 26 be small and lightweight, for reasons discussed in reference to the imaging device 12, above. The illumination system 26 can be mounted on the imaging device 12, on the outer surface of an imaging device enclosure 11, or within an imaging device enclosure 11, which is described hereafter.

The imaging device 12 and optional illumination system 26 can be unenclosed or enclosed. Preferably, the imaging device 12 is enclosed in an imaging device enclosure 11 for protection against the environment of packing and processing plants. It is important for the imaging device enclosure 11 to provide a first aperture 13 for the lens of the imaging device 12 to observe the meat 10. If an optional illumination system 26 is used, the illumination system 26 can be mounted either on the outer surface of the imaging device enclosure 11 or within the imaging device enclosure 11. If mounted within the imaging device enclosure 11, the illumination system 26 can be mounted on the imaging device 12. If the illumination system 26 is mounted in the imaging device enclosure 11, it is important for an aperture to be provided for illumination of the meat 10, either the first aperture 13 used by the lens of the imaging device 12 or a second aperture. In either case, the aperture can be unencased or it can be encased by a pane of a transparent material 14, wherein "transparent" is defined as allowing the passage of substantially all of the energy type and wavelength emitted by the illumination system 26 or detectable by the imaging device 12.

If image data is to be transferred from the imaging device 12 to the data processing unit 16 by a transfer cable 44 connected therebetween, it is also important for the imaging device enclosure 11 to provide an aperture 31 for the cable to exit the enclosure. This aperture can be the first aperture 13 used by the lens of the imaging device 12, the second aperture that can be used by the illumination system 26, or a third aperture 31. If the cable exits the enclosure from the first or second aperture, and the first or second aperture is encased by a pane of transparent material 14, it is important to provide a first cable-passage aperture in the pane for passage of the cable. It is preferred that the imaging device enclosure 11 be constructed from a lightweight material and be only large enough to conveniently fit the imaging device 12, and optionally the illumination system 26 described above.

If alternating current is to be used as the power source of the imaging device 12, it is important for an aperture to be provided to pass the power cable from the imaging device 12 to the power source. Any one of the first, second, or third apertures can be used, or a fourth aperture can be used. If the aperture to be used is encased by a pane of transparent material, it is important to provide a second cable-passage aperture in the pane for passage of the power cable. Alternatively, both the power cable and the data-transfer cable can exit the imaging device enclosure through a single cable-passage aperture.

Optionally, the imaging device enclosure can be designed with features to more readily allow user grip and manipulation, e.g. handles, helmet mounting, etc., and/or with features to allow fixing in position without user grip and manipulation, e.g. brackets for wall mounting, ceiling mounting, or tripod mounting, among other features. Optionally, wall, ceiling, or tripod mounting can be to motorized rotatable heads for adjusting imaging device angle and focal length.

Preferably, the imaging device enclosure can be designed to be easily opened to allow for convenient maintenance of the imaging device 12 or replacement of a battery if direct current is used as the power source of the imaging device 12. Maintenance of the illumination system 26 may also be needed, and preferably in this option will be allowed by the same easy-opening design described for the imaging device 12. The easy-opening design can be affected by the use of screws, clamps, or other means widely known in the art. Ease of maintenance is desirable to minimize any downtime that may be encountered.

After image data is captured by the imaging device 12, it is transferred in real-time to the data processing unit 16. Data can be transferred by a transfer cable 14 or by a wireless data transmission device (not shown). In most situations, transfer cable 14 is the preferred medium of transmission based on superior shielding and lower cost. In situations where the imaging device 12 and data processing unit 16 are widely separated, a wireless data transmission device (not shown) can be a more practical medium of transmission. Any technique of data transfer presently known or developed in the future by those of skill in the art can be used.

The video image data can be sent from the video camera 12 to the data processing unit 16 as either analog or digital data. If sent as analog data, it is important to convert the data to digital data before processing by sending the data to a hardware device (not shown) or software module capable of converting the data. Such a hardware module may be termed a "video frame-grabber". If the image data is sent as digital data, no conversion is required before processing the data.

For purposes of the present invention, a "data processing unit" 16 is defined as including, but not limited to, desktop computers, laptop computers, handheld computers, and dedicated electronic devices. Any data processing unit presently known or developed in the future by those of skill in the art can be used in the present invention. In one embodiment of the present invention, the data processing unit 16 can be small and lightweight to provide portability. In a second embodiment of the present invention, the data processing unit 16 can be a microcomputer, minicomputer, or mainframe that is not portable. The present invention is not limited to any specific data processing unit, computer, or operating system. An exemplary embodiment, but one not to be construed as limiting, is a PC- compatible computer running an operating system such as DOS, Windows, or UNIX. The choice of hardware device or software module for conversion of analog data to digital data for use in the present invention is dependent on the imaging device 12, data processing unit 16, and operating system used, but given these constraints the choice will be readily made by one of skill in the art.

Where the imaging device 12 is a visible light sensitive device such as a color camera, it is also preferred that the data processing unit 16 comprises a software module that converts RGB color to L*a*b* color. An exemplary software module for this purpose is sold in HunterLab Color Vision Systems (Hunter Associates Laboratory, Inc.).

In addition to a cable port 46 or a wireless data transmission device (not shown) to receive data from the imaging device 12, it is also preferred that the data processing unit 16 include other input devices, e.g. a keyboard, a mouse or trackball, a lightpen, a touchscreen, a stylus, a bar code reader, etc., to allow convenient exercise of user options in camera and software operation, data processing, data storage, program output, etc.

Figure 3:
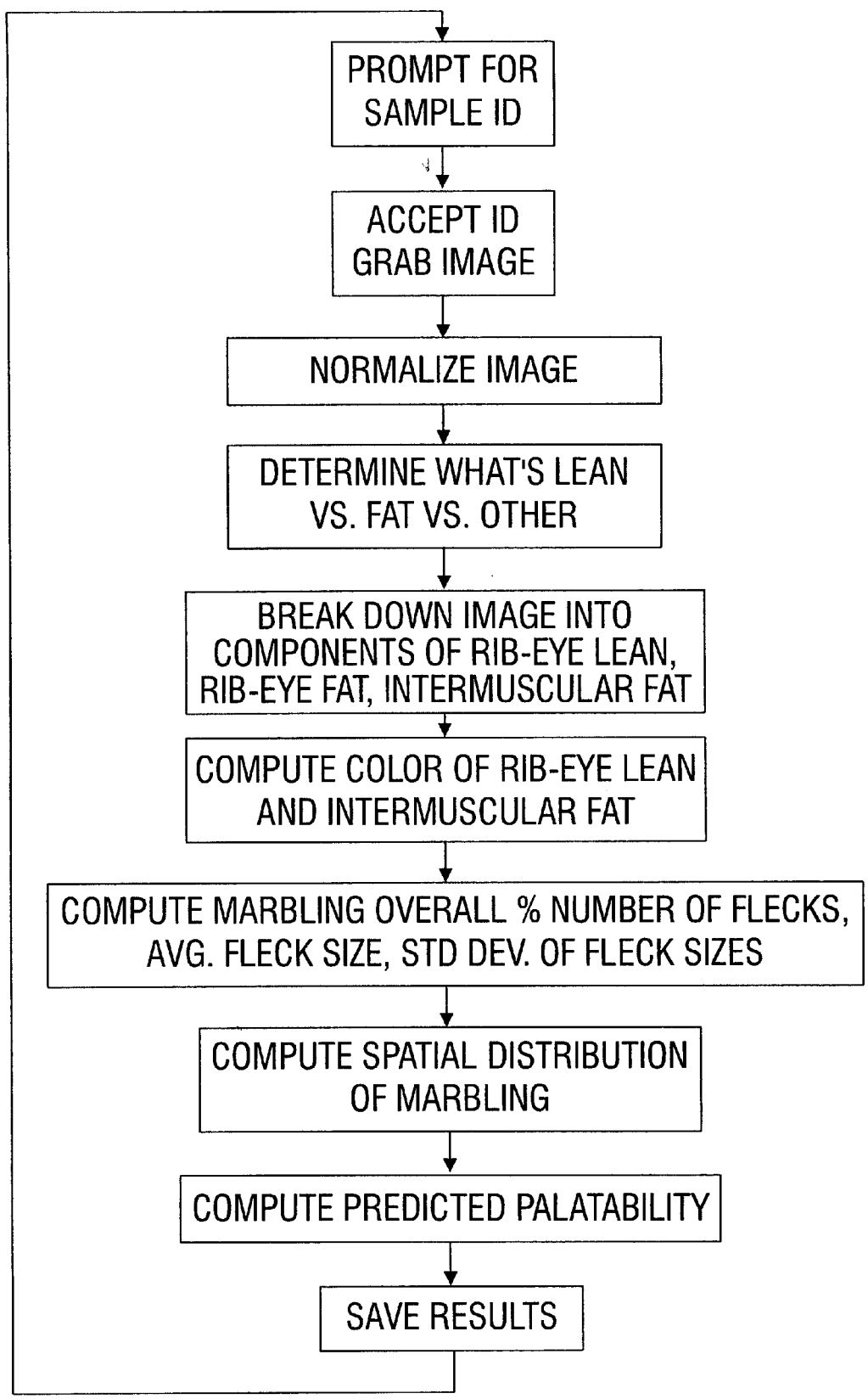
FIG. 3 shows a flowchart of a computer program analyzing image data to distinguish at least one area of interest of the meat, analyzing the image data corresponding to the area of interest to measure at least one characteristic of the area of interest based on the image data.

There are several pieces of software (not shown) which it is important for the data processing unit 16 to store in a program storage device 20 (examples of program storage devices being a hard drive, a floppy disk drive, a tape drive, a ROM, and a CD-ROM, among others), access from the program storage device 20 via program storage device interface 18, and execute. It is important for the data processing unit 16 to have an operating system, and any necessary software drivers to properly control and retrieve data from the imaging device 12 and send output to the at least one output device 24. It is important for the data processing unit 16 to execute a program or programs that can process received image data, calculate various parameters of the muscle imaged in the received image data, and output the results of the calculations to an output device 24. An exemplary code for such a program or programs is given in an appendix hereto. An exemplary flowchart for such a program or programs is given as FIG. 3.

Where the imaging device 12 is a visible light device such as a color camera, the image data can be analyzed for color scale parameters. If it is desired to conform to international standard, the image data can be analyzed for the color scale parameters L*, a*, and b*, as defined by the Commission Internationale d'Eclairage (CIE). A set of L*a*b* parameters is recorded for each frame. L*, a*, and b* are dimensions of a three-dimensional color space which is standardized to reflect how color is perceived by humans. The L* dimension corresponds to lightness (a value of zero being black, a value of 100 being white), the a* dimension corresponds to relative levels of green and red (a negative value being green, a positive value being red), and the b* dimension corresponds to relative levels of blue and yellow (a negative value being blue, a positive value being yellow). In a preferred embodiment, the system can capture pixelated images from areas of 12 to 432 square inches (75 to 2700 cm$^2$) from the muscle of interest, comprising up to 350,000 pixels per measurement, and determine L*, a*, and b* for subregions of the image frame comprising at least one pixel each. In all embodiments, it is desirable for determination of L*a*b* to be performed using the HunterLab software conversion or similar module. Once the value of L*a*b* is determined, at least one of the L*, a*, and b* components can be used in subsequent data processing.

The image data can be further analyzed to identify areas of interest corresponding to factors predictive of palatability using any such methods of analysis known to those of skill in the art, including, among others, image segmentation, histogram thresholding, spatial analysis, pattern matching, pattern analysis, neural network, region growing, and focus of attention methods, as described in numerous references, such as The Image Processing Handbook 3$^{rd}$ Edition, 1999, John C. Russ, CRC Press.

In the preferred embodiment, after determination of L*, a*, and b* for each area of interest, a program then calculates several parameters of the image for each frame. First, the program outlines the muscle of interest by choosing areas that have tolerances of b* compatible with muscle. A sorting of at least one area of the image into one of two classifications, as in muscle and non-muscle, may be termed a "binary mask." Areas with values of b* compatible with the muscle of interest are then examined for their L* and a* scores for verification and rejection of surrounding tissues invading the outline of the muscle of interest. Further examination need not be performed on areas with L*, a*, and b* scores suggestive of bone, connective tissue, and fat. The surface area of the cross-section of the muscle of interest is determined.

Within the portion of the image taken from the muscle of interest, the lean tissue and fat tissue of the muscle can be distinguished and raw L*, a*, and b* scores, and variation in L*, a* and b* scores across the area of interest, for the lean tissues of the muscle can be determined. These scores can then be sent to the output device 24 to be displayed in numerical format and/or retained to calculate quality- and yield-determining characteristics as described below. It is known that, among other characteristics, higher values of b* for lean tissues of muscle correlate with greater tenderness (Wulf et. al., 1996). In addition, the fat color and color variability of intermuscular fat can also be determined.

Also within the portion of the image taken from the muscle of interest, determinations can be made of the quantity, distribution, dispersion, texture, and firmness of marbling (intramuscular fat deposited within the muscle). The quantity of marbling can be determined by calculating the percentage of muscle surface area with L*, a*, and b* scores compatible with fat tissue.

In addition to calculating the quantity of marbling present, the distribution and dispersion of marbling can be determined. First, the portion of the image derived from the muscle of interest can be divided into subcells of equal size. A size of 64×48 pixels can be used. Within each subcell, the number of marbling flecks can be determined as the number of discrete regions with L*, a*, and b* values corresponding to fat, and the average number of marbling flecks per subcell can be calculated. The variance of numbers of marbling flecks across all subcells can be calculated as well.

In addition, the average size of each marbling fleck can be determined throughout the muscle of interest from the number of pixels within each discrete region with L*, a*, and b* values corresponding to fat. The variance of marbling size across all marbling flecks can be calculated as well. The texture and fineness of marbling can also be measured. It is well known that generally, greater amounts of more uniformly distributed and finer-textured marbling reflect a higher marbling score and thus meat of higher eating quality.

Also, the program can use L*, a*, and b* data to calculate the average texture, i.e. cross- sectional surface roughness, of the muscle, and also the firmness of the lean tissue of the cross- sectional muscle. It is well known that the surface roughness of a muscle is inversely correlated with tenderness, and greater firmness is correlated with flavorfulness.

In systems wherein the imaging device 12 is a sound wave imager, tomographic imager, magnetic resonance imager, radio wave imager, microwave imager, or particle beam imager, the program can determine the density of the lean tissue, the density of the fat tissue and the density of the connective tissue.

To summarize, characteristics of the area of interest of the meat 10 that can be measured include, but are not limited to, the color of the lean tissue, the color variation of the lean tissue, the color of fat tissue, the color variation of the fat tissue, a marbling quantity, a marbling distribution, a marbling dispersion, a marbling texture, a marbling fineness, an average texture of the lean tissue, a firmness of the lean tissue, a surface area of the lean section, the density of the lean tissue, the density of the fat tissue and the density of the connective tissue. Quantities of the non-lean section of the meat 10, including but not limited to the color of fat, the density of the lean tissue, the density of the fat tissue, the density of the connective tissue and the relative areas of cross-section surfaces comprised of fat, bone, and/or connective tissue, may be calculated as well. Other characteristics that one of skill in the art of meat science can readily see may be calculated from the values of L*, a*, and b* and that can be predictive of palatability can be calculated by the program, and any such characteristics are considered to be within the scope of the present invention.

Once values of the several parameters described above are calculated, the program can output to the output device 24 calculated values of any or all of the characteristics given above: color of lean tissue, color variation of lean tissue, color of fat tissue, color variation of fat tissue, extent of marbling, average number of marbling flecks per unit area, variance of marbling flecks per unit area, average size of marbling, variance of the average size of marbling, texture and fineness of marbling, average texture of lean tissue, firmness of lean tissue, the density of the lean tissue, the density of the fat tissue and the density of the connective tissue. Preferably, the calculated values of the characteristics, if output, are displayed as alphanumeric characters that can be conveniently read by the operator. Alternatively, or in addition, to outputting values of characteristics to an output device 24, further calculations can be performed using at least one of the values, and optionally values of parameters input by the operator, to derive estimated Quality Grades or other overall indices of cooked meat palatability, which can then be output.

Further, other parameters not determinable by means of analyzing the image data may be used to augment the characteristics determined from the image data, including, but not limited to, pH, connective tissue quantity, connective tissue solubility, sarcomere length, protease enzymatic activity, calcium measure, electrical impedance, electrical conductivity, and tissue density. These additional characteristics of the meat may be used singly or in combination to improve the accuracy of prediction of palatability over that obtained solely using characteristics measured from the image data.

In addition, because a specific muscle of interest has been isolated in a cross-sectional image, and the geometry and distance of the apparatus relative to the meat 10 can be known, the area of the cross-sectional surface of the muscle portion of the meat 10 can be calculated and output to the output device 24. Alternatively, or in addition, to outputting the area to an output device 24, further calculations can be performed using the area of the cross-sectional surface of the muscle, other parameters readily seen by one of skill in the art of meat science as calculable from the L*a*b* data, other image-derived parameters, or values of parameters input by the operator, to derive estimated Yield Grades or other overall indices of composition of the meat 10.

Further, other parameters not determinable by means of analyzing the image data may be used to augment the characteristics determined from the image data, including, but not limited to, subcutaneous fat depth. These additional characteristics of the meat may be used singly or in combination to improve the accuracy of prediction of Yield Grades over that obtained solely using characteristics measured from the image data.

The results reported by the program can be output to any output device 24, such as a screen, printer, speaker, etc. If operator evaluation of the results is desired, results can preferably be displayed on a screen. Preferably, the screen is readily visible to the grader, evaluator, or operator at his or her stand. Alternatively, or in addition, it is preferable that results be printed or output in such a manner that the outputted- results can be transferred and affixed to the meat 10. The manner for outputting results can be text, symbols, or icons readable by personnel either in the packing plant or at later points in the meat production system. Alternatively, the manner for outputting results can be a barcode or other object that can be read by appropriate equipment and decoded into forms readable by personnel at various points in the production system. Output results can be affixed to the meat 10 by methods well-known to the art, which include, but are not limited to, pins, tacks, and adhesive.

The power source 50 of the data processing unit 16 can be either direct current, i.e. a battery, or alternating current drawn from an electrical outlet.

In the embodiment wherein the data processing unit 16 is dedicated for use in the present apparatus, the data processing unit 16 can be mounted in a data processing unit enclosure 15 or in the imaging device enclosure 11, or can be unenclosed. In the embodiment wherein the data processing unit 16 is a microcomputer, minicomputer, or mainframe computing resource present in the plant or facility where the apparatus is used, enclosure is not required. In the embodiment wherein the data processing unit 16 is a separate, stand-alone, portable entity, preferably the data processing unit 16 is mounted in a data processing unit enclosure 15.

It is important for the data processing unit enclosure to provide an aperture 47 or apertures for output of data to or display of data by the output device 24. For example, if display is to be performed using a video screen congruent with the data processing unit 16, it is important for the data processing unit enclosure to provide an aperture 47 for observation of the video screen therethrough. Such an aperture can be unencased or it can be encased by a pane of transparent material 48, such as glass, plastic, etc. If display is to be performed by an external device, e.g. a remote monitor or printer, it is important for the data processing unit enclosure to provide an aperture (not shown) for passage of an output cable 22 therethrough. If the data processing unit 16 is powered by alternating current, it is important for the data processing unit enclosure 15 to provide an aperture 49 for passage of a power cable therethrough. If it is desired to store outputs to an internal floppy disk drive (not shown), it is important for the data processing unit enclosure 15 to provide an aperture (not shown) for insertion and removal of floppy disks into and from the internal floppy disk drive therethrough. If it is desired to store outputs to an external program storage device 20, it is important for data processing unit enclosure 15 to provide an aperture 19 for passage of a data-transfer cable 18 therethrough.

Preferably, if the data processing unit 16 is a dedicated stand-alone unit, the data processing unit enclosure 15 is only large enough to conveniently fit the data processing unit 16, and is lightweight. Optionally, the data processing unit enclosure 15 can be designed with features to more readily allow user manipulation, e.g. handles. In this embodiment, it is also preferred that the data processing unit enclosure 15 be amenable to easy opening to allow for convenient maintenance of the data processing unit 16. The easy-opening design can be affected by means described for the camera enclosure supra.

The apparatus described above can be used in methods for predicting the palatability, yield, and/or defect conditions of, or augmenting the assignment of USDA or other international grade standards to, meat animal carcasses or cuts, or for sorting for other purposes (e.g. brand names, product lines, etc.). The first step involves collecting image data from the meat 10 using the imaging device 12. The second step involves processing the image data using the data processing unit 16. The third step involves using the results of the processing step in reporting quality-determining characteristics that can be used to augment USDA graders in the assignment of USDA Quality Grades, in reporting the areas of cross-sectional muscle surfaces that can be used to augment USDA graders in the assignment of USDA Yield Grades or other international grade standards, in reporting meat defect conditions, or in sorting the meat 10 based on specific requirements of, for example, a brand-name or product line program. Using this method, the grader or operator's limited time to analyze the meat 10 can be focused on examining parameters most readily examined by a person, providing the grader or operator with more data for each sample of meat 10 in the same amount of time, and allowing more accurate prediction of palatability and assignment of Quality Grade and Yield Grade than is currently possible. In addition, this method allows required computations to be performed more quickly and accurately than is currently possible.

The following example is included to demonstrate a preferred embodiment of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Segregation of Beef Carcasses with Very Low Probabilities of Tenderness Problems A population of 324 beef carcasses was examined in an effort to segregate a subpopulation of carcasses with very low probabilities (<0.0003) of having ribeye shear force values of 4.5 kg or greater and subsequent unacceptably tough-eating cuts. Of the 324 carcasses, 200 were certified to meet the above standard for tenderness.

Of the 324 head, 17 head were preselected for the tender subpopulation on the basis of expert-determined (beef scientist or USDA Grading Supervisor) marbling scores of Modest, Moderate, or Slightly Abundant, the three highest degrees of marbling in the United States Standards for Grades of Carcass Beef.

In a second preselection step, 41 head of the remaining 307 were preselected on the basis of L*a*b* color. These carcasses exhibited a second principle component of lean L*, a*, and b* values of less than −0.70. Such low values of the combined variable have been observed to consistently indicate sufficient tenderness of the subsequent scooked lean.

Third, 19 of the remaining 266 head were preselected on the basis of marbling distribution. Marbling distribution was determined, and the variance of marbling distribution was calculated, by an apparatus of the present invention. A variance of marbling distribution of less than 1.1 has been observed to consistently indicate sufficient tenderness of the subsequent cooked lean (i.e. a shear force value of less than 4.5 kg).

In the final step, tenderness values for each of the remaining 247 head were predicted using a multiple regression equation using CIE a* values for lean and fat, as well as machine measured marbling percentage squared. The multiple regression equation determined that 123 out of 247 carcasses were predicted to have a probability of being not tender of 0.0003. These 123 carcasses were then segregated with the 77 that had been preselected, and certified as being tender. The remaining carcasses had a normal probability of 0.117 of having shear force values in excess of 4.5 kg.

The results indicate that the system is able to segregate groups of beef carcasses having very low probabilities of unacceptable toughness, where current grading methods cannot perform this segregation adequately. This improved sortation increases the economic value of tender carcasses which would have been graded lower by current methods.

Both the apparatus and methods disclosed and claimed herein can be made and executed without undue experimentation in light of the present disclosure. While the apparatus and methods of this invention have been described in terms of preferred embodiments, it will be apparent to those of skill in the art that variations can be applied to the apparatus and methods without departing from the scope of the present claims.

What is claimed is:

1. A method for predicting the palatability of meat comprising the steps of: obtaining at least one image of a specimen of meat; analyzing said at least one image to identify at least one area of interest of said specimen of meat; analyzing said at least one area of interest to determine at least one characteristic of said specimen of meat; and predicting the palatability of said specimen of meat based on said at least one characteristic.

2. The method of claim 1, wherein said at least one image is obtained by at least one of a camera, tomographic imaging device, magnetic resonance imaging (MRI) device, sound wave imaging device, radio wave imaging device, microwave imaging device, or particle beam imaging device.

3. The method of claim 2, wherein said at least one camera is at least one of a photographic camera, a digital still camera, and a video camera.

4. The method of claim 2, wherein said at least one camera responds to light in at least one segment of the light spectrum.

5. The method of claim 4, wherein said at least one segment of the light spectrum comprises ultraviolet wavelengths, visible wavelengths, infrared wavelengths, or portions thereof.

6. The method of claim 2, wherein at least one tomographic image is obtained by x-ray tomography or particle beam tomography.

7. The method of claim 2, wherein at least one sound wave image is obtained by ultrasound, B-mode ultrasound, or infrasonic imaging.

8. The method of claim 1, wherein said analysis to identify at least one area of interest is by at least one of image segmentation, histogram thresholding, spatial analysis, pattern matching, pattern analysis, neural network, region growing, and focus of attention methods.

9. The method of claim 8, wherein said analysis to identify at least one area of interest is performed in at least one image plane.

10. The method of claim 1, wherein said at least one characteristic comprises at least one of the color of the lean tissue, the color variation of the lean tissue, the color of the fat tissue, the color variation of the fat tissue, a marbling quantity, a marbling distribution, a marbling dispersion, a marbling texture, a marbling fineness, an average texture of the lean tissue, a firmness of the lean tissue, a surface area of the area of interest, a length of the area of interest, a width of the area of interest, density of the lean tissue, density of the fat tissue, and density of the connective tissue.

11. The method of claim 1, further comprising determining at least one non-image characteristic of said specimen of meat; and predicting the palatability of said specimen of meat based on said at least one characteristic determined from said at least one image, in combination with said at least one non-image characteristic.

12. The method of claim 11, wherein said at least one non-image characteristic comprises at least one of pH, connective tissue quantity, connective tissue solubility, sarcomere length, protease enzymatic activity, calcium measure, electrical impedance, electrical conductivity, and tissue density.

13. The method of claim 1, further comprising determining a Quality Grade for the meat based on said at least one characteristic.

14. The method of claim 1, further comprising determining a Yield Grade for the meat based on said at least one characteristic.

15. The method of claim 14, further comprising determining at least one non-image characteristic of said specimen of meat; and determining a Yield Grade for the meat based on said at least one characteristic determined from said at least one image, in combination with said at least one non-image characteristic.

16. The method of claim 1, further comprising determining defect conditions for the meat based on said at least one characteristic.

17. The method of claim 16 wherein said defect conditions include at least one of bruising, dark cutter or heat ring.

18. The method of claim 1 wherein said prediction of palatability includes calculating at least one of the L*, b*, or a* color components of the specimen.

19. The method of claim 1 wherein said at least one characteristic comprises at least one of the color variation of the lean tissue, the color variation of the fat tissue, a marbling distribution, a marbling texture, a marbling fineness, an average texture of the lean tissue, or a firmness of the lean tissue.

20. The method of claim 1, wherein said at least one image is obtained by at least one tomographic imaging device, magnetic resonance imaging (MRI) device, radio wave imaging device, microwave imaging device, or particle beam imaging device.

21. An apparatus for predicting the palatability of meat, comprising at least one imaging device for obtaining at least one image of a specimen of meat; a data processing unit adapted to execute program instructions; a program storage device encoded with program instructions that, when executed, perform a method for predicting the palatability of meat, the method comprising: analyzing said at least one image to identify at least one area of interest of said specimen of meat; analyzing said at least one area of interest to determine at least one characteristic of said specimen of meat; and predicting the palatability of said specimen of meat based on said at least one characteristic.

22. The apparatus of claim 21, wherein said at least one imaging device is at least one of a camera, a tomographic imager, a magnetic resonance imager, a sound wave imager, a radio wave imager, a microwave imager, and a particle beam imager.

23. The apparatus of claim 22, wherein said at least one camera is at least one of a photographic camera, a digital still camera, and a video camera.

24. The apparatus of claim 22, wherein said at least one camera responds to light in at least one segment of the light spectrum.

25. The apparatus of claim 24, wherein said at least one segment of the light spectrum comprises ultraviolet wavelengths, visible wavelengths, infrared wavelengths, or portions thereof.

26. The apparatus of claim 22, wherein at least one tomographic imager is at least one of an x-ray tomographic imager or a particle beam tomographic imager.

27. The apparatus of claim 22, wherein at least one sound wave imager is at least one of an ultrasound imager, a B-mode ultrasound imager, or an infrasonic imager.

28. The apparatus of claim 21, wherein said at least one area of interest is identified by at least one of image segmentation, histogram thresholding, spatial analysis, pattern matching, pattern analysis, neural network, region growing, and focus of attention methods.

29. The apparatus of claim 28, wherein said analysis to identify at least one area of interest is performed in at least one image plane.

30. The apparatus of claim 21, wherein said at least one characteristic comprises at least one of the color of the lean tissue, the color variation of the lean tissue, the color of the fat tissue, the color variation of the fat tissue, a marbling quantity, a marbling distribution, a marbling dispersion, a marbling texture, a marbling fineness, an average texture of the lean tissue, a firmness of the lean tissue, a surface area of the area of interest, a length of the area of interest, a width of the area of interest, density of the lean tissue, density of the fat tissue, and density of the connective tissue.

31. The apparatus of claim 21, wherein the method further comprises determining at least one non-image characteristic of said specimen of meat; and predicting the palatability of said specimen of meat based on said at least one characteristic determined from said at least one image, in combination with said at least one non-image characteristic.

32. The apparatus of claim 31, wherein said at least one non-image characteristic includes at least one of pH, connective tissue quantity, connective tissue solubility, sarcomere length, protease enzymatic activity, calcium measure, electrical impedance, electrical conductivity, and tissue density.

33. The apparatus of claim 21, wherein the method further comprises determining a Quality Grade for the meat based on said at least one characteristic.

34. The apparatus of claim 21, wherein the method further comprises determining a Yield Grade for the meat based on said at least one characteristic.

35. The apparatus of claim 34, wherein the method further comprises determining at least one non-image characteristic of said specimen of meat; and determining a Yield Grade for the meat based on said at least one characteristic determined from said at least one image, in combination with said at least one non-image characteristic.

36. The apparatus of claim 21, wherein the method further comprises determining defect conditions for the meat based on said at least one characteristic.

37. The method of claim 36 wherein said defect conditions include at least one of bruising, dark cutter, and heat ring.

38. The method of claim 21 wherein said prediction of palatability includes calculating at least one of the $L^*$, $b^*$, or $a^*$ color components of the specimen.

39. The method of claim 21 wherein said at least one characteristic comprises at least one of the color variation of the lean tissue, the color variation of the fat tissue, a marbling distribution, a marbling texture, a marbling fineness, an average texture of the lean tissue, or a firmness of the lean tissue.

40. The method of claim 21, wherein said at least one image is obtained by at least one tomographic imaging device, magnetic resonance imaging (MRI) device, radio wave imaging device, microwave imaging device, or particle beam imaging device.

41. An apparatus for predicting the palatability of meat, comprising: means for obtaining at least one image of a specimen of meat; means for analyzing said at least one image to identify at least one area of interest of said specimen of meat; means for analyzing said at least one area of interest to determine at least one characteristic of said specimen of meat; and means for predicting the palatability of said specimen of meat based on said at least one characteristic.

42. The method of claim 41 wherein said prediction of palatability includes calculating at least one of the $L^*$, $b^*$, or $a^*$ color components of the specimen.

* * * * *